United States Patent [19]

Smith

[11] 4,168,278

[45] Sep. 18, 1979

[54] METHOD FOR THE PREPARATION OF AMINOAMIDES EMPLOYING ε-CAPROLACTAM

[75] Inventor: Harry A. Smith, Midland, Mich.

[73] Assignee: The Dow Chemical Company, Midland, Mich.

[21] Appl. No.: 926,783

[22] Filed: Jul. 21, 1978

[51] Int. Cl.$^2$ .......................................... C07C 103/50
[52] U.S. Cl. ......................... 260/561 A; 260/562 N; 544/176
[58] Field of Search ........... 260/561 A, 562 N, 239 B; 528/315; 544/176

[56] References Cited

U.S. PATENT DOCUMENTS

| | | | |
|---|---|---|---|
| 2,526,078 | 10/1950 | Kropa | 528/315 |
| 3,114,711 | 12/1963 | Stuart | 252/32.7 E |
| 3,867,405 | 2/1975 | Kanetka | 260/561 A |
| 3,874,869 | 4/1975 | Koppensteiner et al. | 260/561 A |
| 3,892,806 | 7/1975 | Eckert et al. | 260/561 A |

OTHER PUBLICATIONS

Shpital'nyl et al., Chem. Abst. 1954, col. 11329c.
Eckert et al., Chem. Abst. 74(1971), #55503z.
Badische Anilin etc., Chem. Abst. 1953, col. 1730i.
Kirk-Othmer, Encyclopedia of Polymer Science and Technology, vol. 10, (1970), pp. 486-511, 544, 545, 550-553.

*Primary Examiner*—Arthur P. Demers

[57] ABSTRACT

One-to-one adducts of primary or secondary amines with ε-caprolactam are made by heating the reactants in the presence of water at a temperature of between about 170° and 320° C.

8 Claims, No Drawings

METHOD FOR THE PREPARATION OF AMINOAMIDES EMPLOYING ε-CAPROLACTAM

Aminoamides are frequently desirable as depolymerization inhibitors in the preparation of poly-ε-caprolactams. Such aminoamides are also desirable as chemical intermediates in the preparation of surfactants by quaternization of the amine group to provide cationic surfactants. A particularly convenient source of raw materials for aminoamides is the addition of a primary or secondary amine to ε-caprolactam. Attempts at such addition are set forth by U.S. Pat. No. 2,526,078. Kropa and Padbury were not successful in isolating any of the one-to-one adducts of an amine and ε-caprolactam. They obtained low-molecular weight adducts which contained an average of more than two to about sixteen ε-caprolactam units per molecule. Products obtained by Kropa and Padbury were indicated to be useful as plasticizers.

It would be desirable if there were available an improved method for the preparation of a one-to-one adduct of a primary or secondary amine and ε-caprolactam.

It would also be desirable if such a method were simple and provided high yields.

These benefits and other advantages in accordance with the present invention are obtained in a method for the preparation of an aminoamide wherein a primary or secondary amine of the Formula (I):

where $R_1$ and $R_2$ are individually selected from the group consisting of hydrogen, alkyl radicals, cycloalkyl radicals, hydroxyalkyl radicals, alkylsulfide radicals, hydroxyalkylsulfide radicals, amidoalkyl radicals, amidohydroxyalkyl radicals, aromatic radicals, ar-alkyl radicals, alkaryl radicals and carboxyalkylsulfide radicals, such radicals containing up to 18 carbon atoms where $R_1$ and $R_2$ are collectively considered, $R_1$ and $R_2$ is divalent alkylene or a bisalkylene ether and mixtures thereof and ε-caprolactam in the presence of at least 0.05 mole of water per mole of amine, the amine being present in a quantity of from about 0.7 to 1.5 moles of amine per mole of ε-caprolactam, heating the mixture of amine, ε-caprolactam and water in an inert atmosphere to a temperature of between about 170° and 320° C. to obtain a compound of the Formula:

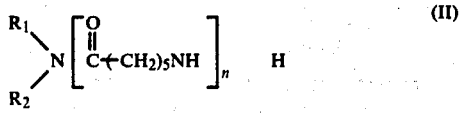

wherein $R_1$ and $R_2$ have previously stated values and "n" has an average value of from about 0.7 to a value of less than 2.

In the practice of the present invention, ε-caprolactam of commercial purity is satisfactory. The amine employed may be a free amine or in the form of an amine salt of an organic or inorganic acid as such salts disassociate when subjected to process conditions. Generally, the amine is added prior to heating the reaction mixture to the desired processing temperature. However, in most cases it is preferred to add the amine prior to heating to the processing temperature. The reaction may be conveniently carried out in agitated pressure vessels of nickel and stainless steel, nickel being preferable to stainless steel. Generally, it is desirable to agitate the reaction mixture and exclude oxygen from the system prior to reaching the reaction temperature. Beneficially, one of the more convenient manners of excluding oxygen is to purge the vessel with nitrogen, argon or like inert gases prior to heating. In the event low boiling amine is employed such as methyl amine, it is desirable to purge the vessel containing the ε-caprolactam and water and subsequently add the amine. The reaction temperature employed may be from about 170° to 320° C., however, it is preferable to conduct the reaction at a temperature of about 200° to 300° C. When the reaction temperature is below 170° C., the reaction rate is inconveniently slow and if the temperature is in excess of about 320° C., yields are substantially reduced as it is believed the product is hydrolyzed. Low boiling amines require larger quantities of water than do higher boiling amines. By the term "low boiling amines" is meant amines which boil below 160° C. under atmospheric pressure. The minimum quantity of water required to obtain an adduct where the average value of "n" is less than two, for low boiling amines, is obtained from the equation: moles of water per mole of amine equals $-0.012 \times$(amine boiling point °C.)$+1.92$. An excess of water up to twenty times the minimum may be employed. When the boiling point of the amine is in excess of 160° C. at atmospheric pressure, the amount of water per mole of amine generally can be from 0.05 to 0.1. Generally within the temperature range of 200° to 300° C., the reaction time can be from about 4 to 24 hours and preferably from about 12 to 14 hours. The reaction is conducted under autogenous pressure and when complete is vented and the temperature lowered to 100° C. and a nitrogen purge can be employed to remove unreacted starting materials. The products of the invention are generally low melting solids, that is, melt between about 50° and 100° C. and as recovered from a stainless-steel reactor are pasty grey solids. The products directly from the reactor are of sufficient purity for preparation of surfactant or for use as nylon depolymerization inhibitors.

The invention is further illustrated but not limited by the following examples wherein n is the average value of n of Formula II.

EXAMPLE 1

A mixture of 11.3 grams (0.1 mole) of ε-caprolactam and 7.5 grams (0.1 mole) of isopropanolamine and 0.2 gram (0.011 mole) of water was sealed in a 45-milliliter Parr bomb in a nitrogen atmosphere. The mixture in the Parr bomb was heated to a temperature of 250° C. for a period of twelve hours. The pressure in the reactor was 45 pounds per square inch guage. At the end of the twelve-hour period, the reactor was cooled and 19.0 grams of an off-white paste was obtained which was analyzed by means of nuclear magnetic resonance and gas chromatography. The paste contained 13.5 weight percent isopropanolamine and 5.3 weight percent ε-caprolactam. In the resultant compound $R_1$ was H and $R_2$ was 2-hydroxypropyl. The average value of "n" was 1.38. The product contained 72.5 weight percent of the one-to-one additive where n=1 and the amine equivalent weight was 231.

EXAMPLE 2

The procedure of Example 1 was repeated employing a 2-liter agitated Parr bomb using 565 grams (5 moles) of caprolactam, 9 grams of water (0.5 mole), 375 grams of isopropanolamine (5 moles). The reaction time employed was 11.5 hours; the yield about 96 percent. The product contained 5.1 weight percent $\epsilon$-caprolactam, 8.5 weight percent isopropanolamine. The average "n" was 1.16 and the amine equivalent weight 206. The product contained 86.2 weight percent of compound wherein n=1. The foregoing procedure was repeated with the exception that the reaction time was 14 hours instead of 11½ hours. The yield was about 96 percent, $\epsilon$-caprolactam content was 5 weight percent, isopropanolamine 6.6 percent. The average "n" was 1.1. The amine equivalent weight 199 and the product contained about 90.9 weight percent of adduct wherein "n" was 1. A third reaction was run for a total of 18 hours and was 5.1 percent residual $\epsilon$-caprolactam, 7 weight percent residual isopropanolamine. The average value for "n" was 1.11 and 89 percent of the product had a value of n=1. The amine equivalent weight was 200.

EXAMPLE 3

A plurality of runs were made in a 2-liter agitated stainless steel Parr bomb employing 232.5 (2.1 moles) grams of $\epsilon$-caprolactam, 187.5 grams (2.5 moles) of isopropanolamine and varying amounts of water. The results are set forth in the following Table. Under the column "Mole Ratio" is the mole ratio of water to $\epsilon$-caprolactam as initially charged. Under "$\epsilon$-Caprolactam" and "Mono-Isopropanolamine" are the weight percents in the final product. "n" is the average value of n.

Table I

| Run | Mole Ratio* | Reaction Time Hours | Percent $\epsilon$Caprolactam | Percent Mono-Isopropanol-Amine | Amine "n" | Equivalent Weight |
|---|---|---|---|---|---|---|
| 1 | 1/20 | 12 | 5.5% | 8.8% | 1.16 | 206 |
| 2 | 1/10 | 12 | 5.1% | 8.5% | 1.16 | 206 |
| 3 | 1/5  | 12 | 5.2% | 8.1% | 1.15 | 205 |

*Water to caprolactam

EXAMPLE 4

The procedure of Example 3 was repeated with the exception that the ratio of water to $\epsilon$-caprolactam was maintained at 1 to 20 moles and the reaction time varied. The results are set forth in Table II.

Table II

| Run | Mole Ratio | Reaction Time Hours | Percent $\epsilon$-Caprolactam | Percent Mono-Isopropanol-Amine | "n" | Amine Equivalent Weight |
|---|---|---|---|---|---|---|
| 1 | 1/20 | 6  | 5.0% | 11.3% | 1.28 | 220 |
| 2 | 1/20 | 12 | 5.2% | 8.1%  | 1.15 | 205 |
| 3 | 1/20 | 18 | 4.1% | 6.4%  | 1.10 | 199 |

EXAMPLE 5

The procedure of Example 1 was repeated with the exception that 0.1 mole of ammonia as a 28 weight percent aqueous solution was substituted for the isopropanolamine. After 12 hours, the product contained 12.1 percent $\epsilon$-caprolactam, no ammonia, 87.9 weight percent of adduct wherein the average value of n was 1.54. The amine equivalent weight was 191. The ratio of water to $\epsilon$-caprolactam was 2.5 to 1. In the product obtained $R_1$ and $R_2$ were both hydrogen.

EXAMPLE 6

The apparatus of Example 2 was employed using 565 grams (5 moles) of $\epsilon$-caprolactam, and 435 grams (5 moles) or morpholine wherein the mole ratio of water to $\epsilon$-caprolactam was 1:5, in a second run 1:2 and in a third run 1:1.3. The results are set forth in Table III.

Table III

| Run | Mole Ratio | Percent $\epsilon$-Caprolactam | Percent Morpholine | "n" | Percent n:1 | Amine Equivalent Weight |
|---|---|---|---|---|---|---|
| 1 | 1/5.0 | 8.00% | 32.0% | 3.6  | low   | 495 |
| 2 | 1/2   | 7.8%  | 21.5% | 1.73 | 27.0% | 283 |
| 3 | 1/1.3 | 6.8%  | 18.1% | 1.57 | 43.0% | 264 |

COMPARATIVE EXAMPLE

The procedure of Example 1 was repeated with the exception that alcohols were substituted for the amine and the ratio of alcohol to lactam was 1:1. Table IV sets forth the results.

Table IV

| Run | Alcohol | Mole Ratio | Reaction Time Hours | Percent $\epsilon$-Caprolactam | Percent Alcohol | "n" | Amine Equivalent Weight |
|---|---|---|---|---|---|---|---|
| (Primary OH) | | | | | | | |
| 1 | Lauryl | 1/10 | 18 | 12.0% | 47.7% | 2.88 | 511 |
| 2 | Lauryl | 1/5  | 20 | 9.9%  | 38.4% | 1.94 | 405 |
| (Secondary OH) | | | | | | | |

Table IV-continued

| Run | Alcohol | Mole Ratio | Reaction Time Hours | Percent ε-Caprolactam | Percent Alcohol | "n" | Amine Equivalent Weight |
|---|---|---|---|---|---|---|---|
| 3 | TPME* | 1/5 | 12 | 23.4% | 57.6% | 3.4 | — |

*Tripropylene glycol methyl ether

EXAMPLE 7

The procedure of Example 1 was repeated wherein the isopropanolamine was replaced with a molar equivalent of aminoethyloctyl sulfide. The product contained 4.3 weight percent ε-caprolactam, 19.7 percent aminoethyloctyl sulfide and 76 weight percent of an adduct wherein the average "n" was 1.32. The amine equivalent weight was 327. The molar ratio of water to amine in the initial reaction was 0.1:1.

EXAMPLE 8

The procedure of Example 1 was repeated using a molar equivalent of ispopropylamine instead of isopropanolamine. 0.72 Gram of water was employed to give a water to ε-caprolactam molar ratio of 1.6:1. The product contained 24.2 weight percent ε-caprolactam, 2 weight percent isopropylamine, 73.8 weight percent of an adduct having an average value of n of 0.92. The amine equivalent weight was 163.

EXAMPLE 9

The procedure of Example 2 was repeated with the exception that the reaction time was four hours and temperatures in different runs were varied from 170° to 270° C. The results are set forth in Table V.

Table V

| Reaction Temperature | Percent Conversion Isopropanol Amine | Percent Conversion ε-Caprolactam |
|---|---|---|
| 170° C. | 20.3 | 20.2 |
| 185 | 23.0 | 27.5 |
| 220 | 73.0 | 79.9 |
| 250 | 74.4 | 90.8 |
| 270 | 82.9 | 92.7 |

EXAMPLE 10

The procedure of Example 2 was repeated wherein one run was a blank, one run contained one mole percent phosphoric acid and one run contained one mole of zinc chloride. The results are set forth in Table VI.

Table VI

| Catalyst | Percent Conversion Isopropanol Amine | Percent Conversion ε-Caprolactam |
|---|---|---|
| None | 74.4 | 90.8 |
| H₃PO₄ | 85.8 | 91.0 |
| 2nCl₂ | 87.6 | 93.7 |

EXAMPLE 11

The procedure of Example 2 was repeated using a variety of amines and varying levels of water. The reaction time was 18 to 20 hours at a temperature of 250° C. The results are set forth in Table VII.

Table VII

| Amine | Amine B.P. (°C.) | H₂O/ Amine | Percent ε-Caprolactam | Percent Amine | "n" |
|---|---|---|---|---|---|
| NH₃ | −33 | 2.4/1 | 12.1 | 0 | 1.54 |
| Isopropyl Amine | 33 | 1.6/1 | 24.2 | 6.7 | 0.92 |
| Morpholine | 128 | 0.5/1 | 7.8 | 21.5 | 1.73 |
| Morpholine | | 0.2/1 | 8.0 | 32.6 | 3.6 |
| Isopropanol Amine | 160 | 0.2/1 | 4.7 | 6.4 | 1.10 |
| | | 0.1/1 | 5.1 | 7.0 | 1.11 |
| | | 0.05/1 | 5.5 | 8.8 | 1.16 |
| Aminoethyl-octyl Sulfide | 315 | 0.1/1 | 4.3 | 19.7 | 1.32 |

In a manner similar to the foregoing illustrations adducts of primary and secondary amines with ε-caprolactam are readily prepared.

As is apparent from the foregoing specification, the present invention is susceptible of being embodied with various alterations and modifications which may differ particularaly from those that have been described in the preceding specification and description. For this reason, it is to be fully understood that all of the foregoing is intended to be merely illustrative and is not to be construed or interpreted as being restrictive or otherwise limiting of the present invention, excepting as it is set forth and defined in the hereto-appended claims.

What is claimed is:

1. A method for the preparation of an aminoamide wherein a primary or secondary amine of the Formula (I):

where $R_1$ and $R_2$ are individually selected from the group consisting of hydrogen, alkyl radicals, cycloalkyl radicals, hydroxyalkyl radicals, alkylsulfide radicals, hydroxyalkylsulfide radicals, amidoalkyl radicals, amidohydroxyalkyl radicals, aromatic radicals, ar-alkyl radicals, alkaryl radicals and carboxyalkylsulfide radicals, such radicals containing up to 18 carbon atoms where $R_1$ and $R_2$ are collectively considered, $R_1$ and $R_2$ is divalent alkylene or a bisalkylene ether and mixtures thereof and ε-caprolactam in the presence of 0.05 to 20 moles of water per mole of amine, the amine being present in a quantity of from about 0.7 to 1.5 moles of amine per mole of ε-caprolactam, heating the mixture of amine, ε-caprolactam and water in an inert atmosphere to a temperature of between about 170° and 320° C. to obtain a compound of the Formula (II):

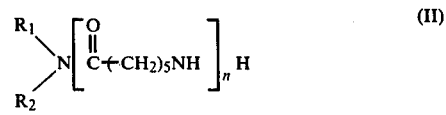

wherein $R_1$ and $R_2$ have previously stated values and "n" has an average value of from about 0.7 to a value of less than 2.

2. The method of claim 1 wherein the inert atmosphere is nitrogen.

3. The method of claim 1 including the step of cooling the mixture to a temperature of about 100° C. and passing nitrogen therethrough to remove unreacted ε-caprolactam and amine.

4. The method of claim 1 wherein the reaction temperature is from about 200° to 300° C.

5. The method of claim 1 wherein the amine and ε-caprolactam are heated for a period of from about 4 to 24 hours at a temperature between 170° and 320° C.

6. The method of claim 5 wherein the heating is carried out for a period of from about 12 to 14 hours.

7. The method of claim 1 wherein the molar ratio of water to one mole of amine, if the amine boils below 160° C., is from 1 to 20 times −0.012 times the amine boiling point in °C. plus 1.92 and if the amine boils at 160° C. or above, the moles of water per mole of amine is from about 0.05 to 1.

8. A method for the preparation of an aminoamide wherein a primary or secondary amine of the Formula (I):

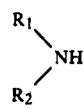

where $R_1$ and $R_2$ are individually selected from the group consisting of hydrogen, alkyl radicals, cycloalkyl radicals, hydroxyalkyl radicals, alkylsulfide radicals, hydroxyalkylsulfide radicals, amidoalkyl radicals, amidohydroxyalkyl radicals, aromatic radicals, ar-alkyl radicals, alkaryl radicals and carboxyalkylsulfide radicals, such radicals containing up to 18 carbon atoms where $R_1$ and $R_2$ are collectively considered, $R_1$ and $R_2$ is divalent alkylene or a bisalkylene ether and mixtures thereof and ε-caprolactam in the presence of 0.05 to 20 moles of water per mole of amine, the amine being present in a quantity of from about 0.7 to 1.5 moles of amine per mole of ε-caprolactam, heating the mixture of amine, ε-caprolactam and water in a nitrogen atmosphere to a temperature of between about 200° and 300° C. for a period of 4 to 24 hours to obtain a compound of the Formula (II):

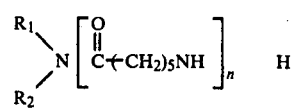

wherein $R_1$ and $R_2$ have previously stated values and "n" has an average value of from about 0.7 to a value of less than 2 cooling the mixture to a temperature of about 100° C. and passing nitrogen therethrough to remove unreacted ε-caprolactam and amine.

* * * * *